(12) United States Patent
Osborne et al.

(10) Patent No.: US 7,563,276 B2
(45) Date of Patent: Jul. 21, 2009

(54) INTRALUMINAL MEDICAL DEVICE WITH CANNULA FOR CONTROLLED RETROGRADE FLOW

(75) Inventors: Thomas A. Osborne, Bloomington, IN (US); Charles W. Agnew, West Lafayette, IN (US); Brian C. Case, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 572 days.

(21) Appl. No.: 11/260,981

(22) Filed: Oct. 28, 2005

(65) Prior Publication Data

US 2006/0106454 A1 May 18, 2006

Related U.S. Application Data

(60) Provisional application No. 60/522,707, filed on Oct. 29, 2004.

(51) Int. Cl.
*A61F 2/06* (2006.01)
(52) U.S. Cl. .................. 623/1.26; 623/2.14; 623/2.16
(58) Field of Classification Search ............. 623/1.24, 623/1.26, 2.12–2.19, 246–249
See application file for complete search history.

(56) References Cited

U.S. PATENT DOCUMENTS

| | | | |
|---|---|---|---|
| 4,328,592 A | 5/1982 | Klawitter | |
| 4,580,568 A | 4/1986 | Gianturco | |
| 5,628,791 A | 5/1997 | Bokros et al. | |
| 5,641,324 A | 6/1997 | Bokros et al. | |
| 5,908,452 A | 6/1999 | Bokros et al. | |
| 6,027,525 A | 2/2000 | Suh et al. | |
| 6,200,336 B1 | 3/2001 | Pavcnik et al. | |
| 6,231,598 B1 | 5/2001 | Berry et al. | |
| 6,287,334 B1 | 9/2001 | Moll et al. | |
| 6,299,635 B1 | 10/2001 | Frantzen | |
| 6,464,720 B2 | 10/2002 | Boatman et al. | |
| 6,482,228 B1 | 11/2002 | Norred | |
| 6,494,909 B2 | 12/2002 | Greenhalgh | |
| 6,508,833 B2 | 1/2003 | Pavcnik et al. | |
| 6,676,698 B2 | 1/2004 | McGuckin, Jr. et al. | |
| 2001/0039450 A1 | 11/2001 | Pavcnik et al. | |
| 2001/0044654 A1* | 11/2001 | Chen et al. | 623/1.41 |
| 2002/0055772 A1 | 5/2002 | McGuckin, Jr. et al. | |
| 2002/0123802 A1* | 9/2002 | Snyders | 623/2.18 |
| 2002/0177894 A1 | 11/2002 | Acosta et al. | |
| 2003/0181974 A1* | 9/2003 | Xie et al. | 623/1.24 |
| 2004/0049262 A1* | 3/2004 | Obermiller et al. | 623/1.15 |
| 2004/0117004 A1* | 6/2004 | Osborne et al. | 623/1.36 |
| 2006/0282157 A1 | 12/2006 | Hill et al. | |

* cited by examiner

*Primary Examiner*—Corrine M McDermott
*Assistant Examiner*—Rebecca Straszheim
(74) *Attorney, Agent, or Firm*—Buchanan Intellectual Property Office LLC

(57) ABSTRACT

Prosthetic valves for regulating fluid flow through a body vessel are described. The valves include a valve member that includes at least a portion that is capable of moving to selectively permit and substantially prevent fluid flow through the body vessel, either alone or with one or more additional valve members. A cannula is associated with the valve and permits a controlled amount of fluid flow through the valve, such as retrograde flow while the valve member substantially prevents fluid flow through the body vessel.

16 Claims, 4 Drawing Sheets

INTRALUMINAL MEDICAL DEVICE WITH CANNULA FOR CONTROLLED RETROGRADE FLOW

CROSS-REFERENCE TO RELATED APPLICATION

This application claims priority to U.S. Provisional Application Ser. No. 60/522,707, filed on Oct. 29, 2004, which is hereby incorporated into this disclosure in its entirety

FIELD

The invention relates to medical devices. More particularly, the invention relates to intraluminal valve prostheses.

BACKGROUND

Many vessels in animal bodies transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction and close to prevent fluid flow in a reverse direction, i.e., retrograde flow. The valves can change from an open position in response to a variety of circumstances, including changes in the cross-sectional shape of the vessel and the fluid pressure within the vessel.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, and can lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed, eliminated, or replaced with autologous sections of veins having competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, the use of stents has been extended to treat aneurysms and to provide occlusion devices, among other uses.

Recently, prosthetic valves that are implantable by minimally invasive techniques have been developed. Frequently, a graft member is attached to a support frame and provides a valve function to the device. For example, the graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, U.S. Patent Application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety. In other examples of prosthetic valves, a tube that terminates in leaflets is attached to one or more support frames to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Natural valves can be somewhat 'leaky', allowing a relatively small quantity of fluid to flow in a reverse direction when the valve is in a closed position. It is believed that this leakiness is beneficial for several reasons. For example, it is believed that a small amount of retrograde flow limits the pooling of blood around the natural valve during periods of low pressure, which can reduce the formation of thrombus adjacent the valve leaflets and, therefore, increase the effective lifetime of the valve.

Prior art prosthetic valves, however, do not permit a controlled amount of retrograde flow. Indeed, most prior art valves have been designed to prevent leakage as much as possible. Accordingly, there is a need for prosthetic valves that permit a controlled amount of retrograde flow.

SUMMARY OF EXEMPLARY EMBODIMENTS

The invention provides implantable medical devices for regulating fluid flow through a body vessel. The devices include one or more cannula that permit a controlled amount of retrograde flow to pass through the device. Exemplary embodiments of the invention relate to prosthetic venous valves.

A medical device according to one exemplary embodiment of the invention comprises a valve member and at least one cannula. At least a portion of the valve member is moveable between first and second positions. In the first position, the valve member permits fluid flow through a body vessel in which the device is implanted. In the second position, the valve member substantially prevents fluid flow through the body vessel in a second, opposite direction. The at least one cannula permits a controlled amount of fluid flow through the device in the second, opposite direction.

In another exemplary embodiment of the invention, a medical device comprises a support frame and at least one cannula. The support frame has radially compressed and radially expanded configurations. The device includes at least one valve member that is attached to the support frame. At least a portion of the at least one valve member is moveable between first and second positions. In the first position, the valve member permits fluid flow through a body vessel in which the device is implanted. In the second position, the valve member substantially prevents fluid flow through the body vessel in a second, opposite direction. Further in the second position, the at least one cannula permits a controlled amount of fluid flow through the device in the second, opposite direction.

The invention also provides methods of implanting medical devices. An exemplary method according to the invention comprises implanting a cannula that defines a lumen and implanting a prosthetic valve at a particular point of treatment within a body vessel. The cannula and valve can be implanted in a single or multiple implantation steps.

The invention also provides kits useful for the treatment of patients. A kit according to an exemplary embodiment comprises a prosthetic valve for regulating fluid flow and at least one cannula. Additional components, such as a delivery device, can also be included.

Additional understanding of the invention can be obtained with review of the description of exemplary embodiments of the invention, appearing below, and the appended drawings that illustrate exemplary embodiments.

DETAILED DESCRIPTION OF EXEMPLARY EMBODIMENTS

The following provides a detailed description of exemplary embodiments. The description is not intended to limit the scope of the invention, or its protection, in any manner, but rather serves to enable those skilled in the art to practice the invention.

The invention provides medical devices that can be used in a variety of applications. For example, medical devices according to exemplary embodiments comprise prosthetic valves that can be used to regulate fluid flow through a body vessel. The prosthetic valves can be implanted in a body vessel, or in any other suitable environment, to regulate the flow of fluid. Valves according to the invention can also be implanted in ducts, canals, and other passageways in the body, as well as cavities and other suitable locations. Valves according to exemplary embodiments of the invention can be implanted in the vessels of the vasculature, such as veins, to regulate the flow of blood through the vessels.

As used herein, the term "implanted," and grammatically related terms, refers to the positioning of an item in a particular environment, either temporarily, semi-permanently, or permanently. The term does not require a permanent fixation of an item in a particular position.

Figure 3:
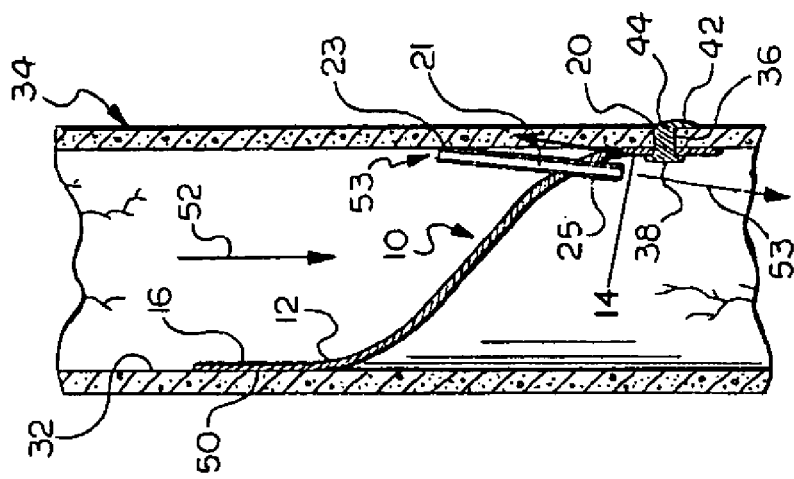
FIG. 3 is a sectional view of a body vessel containing the medical device illustrated in FIG. 1. The medical device is shown in a configuration that substantially prevents fluid flow through the body vessel.
Figure 2:
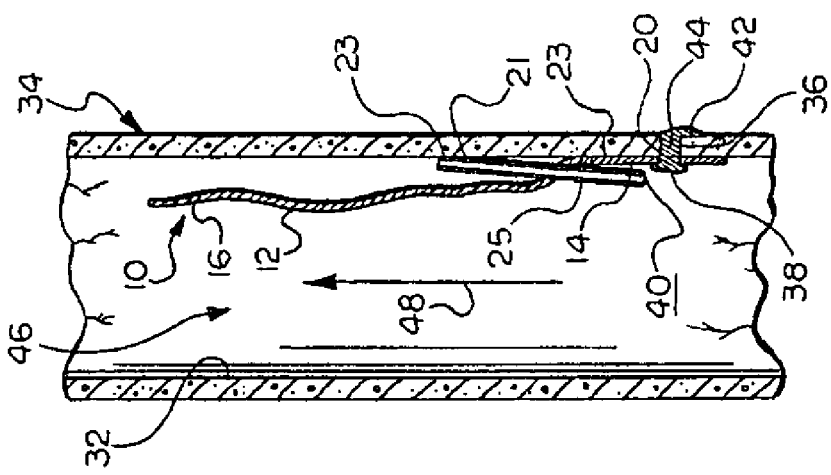
FIG. 2 is a sectional view of a body vessel containing the medical device illustrated in FIG. 1. The medical device is shown in a configuration that allows fluid to flow through the body vessel.
Figure 1:
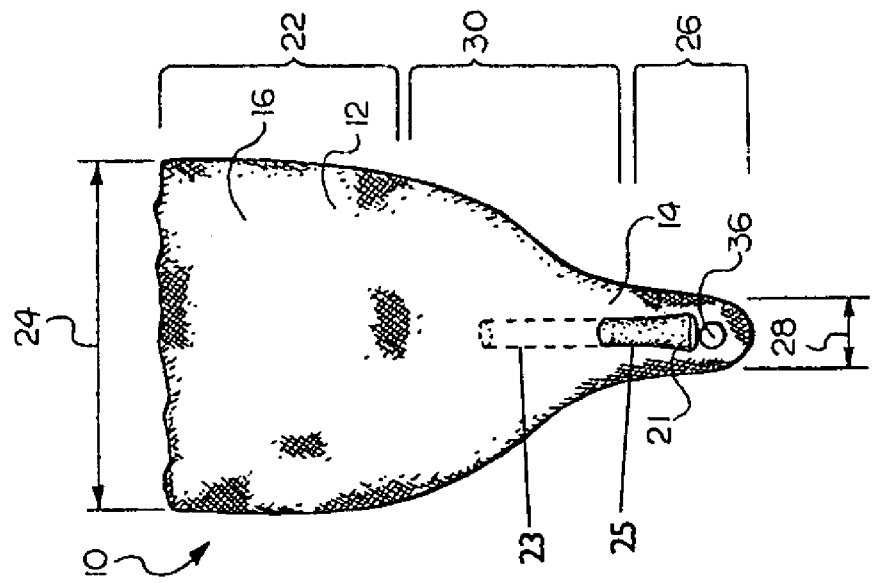
FIG. 1 is a plan view of a medical device according to a first exemplary embodiment.

FIGS. 1 through 3 illustrate a valve 10 according to a first exemplary embodiment of the invention. The valve 10 includes a valve member 12 that has a base portion 14 and a valve portion 16. A cannula 21 is positioned through the valve member 12 at the base portion 14. The valve 10 also includes a means for maintaining an axial position of the valve member 12 and cannula 21 in a body vessel in which the valve 10 is implanted.

Any suitable structure can be used as the means for maintaining an axial position of the valve member 12 and cannula 21 in a body vessel. The specific structure chosen for any particular device according to the invention will depend on several considerations, including the nature of the valve member and the vessel in which the device will be implanted. The structure need only be able to substantially maintain a position of the device on an axis of a vessel in which the device is implanted while fluid flows through the vessel. Examples of suitable structures for the means for maintaining an axial position include barbs, integrally formed anchors, support frames, and their equivalents. In the embodiment illustrated in FIGS. 1 through 3, the means for maintaining an axial position comprise a barb 20 that is structurally distinct from the valve member 12.

The valve member 12 comprises a section of material. The valve member 12 can be formed of any suitable material, and need only be biocompatible or be able to be made biocompatible and be able to perform as described herein. The valve member 12 advantageously can be formed of a flexible material. Examples of suitable materials for the valve member 12 include natural materials, synthetic materials, and combinations of natural and synthetic materials. Examples of suitable natural materials include extracellular matrix (ECM) materials, such as small intestine submucosa (SIS), and other bioremodellable materials, such as bovine pericardium. Other examples of ECM materials that can be used in the medical devices of the invention include stomach submucosa, liver basement membrane, urinary bladder submucosa, tissue mucosa, and dura mater. Examples of suitable synthetic materials include polymeric materials, such as expanded polytetrafluoroethylene and polyurethane. ECM materials are particularly well-suited materials for use in the valve member 12 at least because of their abilities to remodel and to provide a scaffold onto which cellular in-growth can occur, eventually allowing the material to remodel into a structure of host cells.

The cannula 21 passes through the base portion 14 of the valve member 12. The cannula 21 has first 23 and second 25 portions. In the illustrated embodiment, the first portion 23 contacts an inner wall 32 of the body vessel 34, and the second portion 25 does not contact the inner wall 32.

As best illustrated in FIGS. 2 and 3, the valve 10 permits fluid flow through the body vessel 34 in a first direction, represented by arrow 48 in FIG. 2, and substantially prevents fluid flow through the body vessel 34 in a second opposite direction, represented by arrow 52 in FIG. 3. As illustrated in FIG. 3, the cannula 21 allows an amount of fluid to flow through the valve 10 in the second, opposite direction 52. That is, the cannula 21 allows a quantity of retrograde flow, represented by arrows 53 in FIG. 3, to pass through the valve 10 when the valve member 12 is in the closed configuration.

The cannula 21 can have any suitable size and configuration, and the specific size and configuration chosen will depend on several considerations, such as the desired quantity and/or rate of retrograde flow for a particular valve. In exemplary embodiments, the diameter of the cannula 21 is advantageously sized to mimic the degree of retrograde flow—the leakiness—of a natural valve that is typically present at or near a particular point of treatment.

The cannula 21 can be formed of any suitable material, and need only be biocompatible or be able to be made biocompatible and be able to perform as described herein. Examples of suitable materials for the cannula 21 include natural materials, synthetic materials, and combinations of natural and synthetic materials. The specific material used for the cannula 21 can depend on the material used for the valve member 12. For example, in embodiments in which the valve member 12 comprises a bioremodellable material, such as SIS, the cannula 21 can be formed of a resorbable material. This combination of materials is expected to be advantageous at least because the resorbable cannula 21 can be absorbed during or following remodelling of the valve member 12. This will produce an opening in the valve member 12 at the position at which the cannula 21 passed through the valve member 12 prior to absorption. The resulting opening can then allow retrograde flow by the remodelled valve member 12.

The cannula can be coated, impregnated, or otherwise associated with a bioactive agent having desirable properties. For example, to facilitate flow of blood through the cannula in blood valve embodiments, it may be desirable to coat, impregnate, or otherwise associate an antithrombogenic agent with the cannula. This can be particularly advantageous when the cannula has a sufficiently small diameter that might result in restricted fluid flow if a thrombus were to form or become lodged in, on, or around the cannula. Any suitable bioactive agent can be used. Examples of suitable antithrombogenic agents include anticoagulants, such as heparin. Other suitable agents include paclitaxel, polymeric formulations, such as Thoralon-based polymers, and other agents exhibiting an ability to delay, prevent, or inhibit the formation of thrombus. Also, agents that are capable of disrupting a formed thrombus, such as streptokinase, can also be used.

As used herein, the term "resorbable" refers to the ability of a material to be absorbed into a tissue and/or body fluid upon contact with the tissue and/or body fluid. The contact can be prolonged, and can be intermittent in nature. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), and polyglycolide; trimethlyene carbonate; polycaprolactone; poly-beta hydroxy acids such as polyhydroxybutyrate and polyhydroxyvalerate; and other polymers such as polyphosphazines, polyorganophosphazines, polyanhydrides, polyesteramides, polyorthoesters, polyethylene oxide, polyester-ethers (e.g., polydioxanone) and polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

The valve member 12 can have any suitable size and configuration, and the specific size and configuration chosen for the valve member in a particular valve according to the invention will depend on several considerations, including the size, configuration, and/or nature of the vessel in which the valve will be implanted. In the embodiment illustrated in FIGS. 1 through 3, the valve member 12 includes a first portion 22 having a first width 24, and a second portion 26 having a second width 28. The first width 24 is greater than the second width 28. Advantageously, the first portion 22 includes the valve portion 16. Also advantageously, the second portion 26 includes the base portion 14. In the illustrated embodiment, a transition region 30 is disposed between the first 22 and second 26 portions and includes a width that tapers from the first width 24 to the second width 28.

As best illustrated in FIGS. 2 and 3, the base portion 14 provides a portion of the valve member 12 that can be anchored to an inner wall 32 of a body vessel 34 in which the valve 10 is implanted. When the valve 10 is implanted in a body vessel 34, the base portion 14 and cannula 21 remain substantially static, even as fluid flows through the body vessel 34 and cannula 21, because the base portion 14 is associated with a means for maintaining an axial position of a portion of the leaflet 12 in the body vessel. For example, in the illustrated embodiment, the base portion 14 defines an opening 36. Barb 20 is partially disposed in the opening 36, with a head 38 disposed adjacent one surface of the valve member 12 and anchor portion 42 of the barb 20 is disposed external to the body vessel 34. A body portion 44 of the barb 20 is disposed within the opening 36 and through the wall 32 of the body vessel 34. The head 38 and anchor portion 42 of the barb 20 can be compressed toward each other during implantation of the valve 10.

The barb 20 can be formed of any suitable material, and need only be biocompatible or able to be made biocompatible. Also, the barb 20 can have any suitable size and configuration, and the specific size and configuration chosen for any particular valve according to the invention will depend on several considerations, including the nature of the vessel in which the valve is being implanted. Also, the specific material used for the barb 20 can depend on the material used for the valve member 12. For example, in embodiments in which the valve member 12 comprises a bioremodellable material, such as SIS, the barb 20 can be formed of a resorbable material, including the resorbable materials described above.

In embodiments in which the barb 20, or another suitable means for maintaining an axial position of the valve 10, comprises a resorbable material, the base portion 14 of the valve member 12, or a portion thereof, can eventually become incorporated into the wall 32 of the body vessel 34, providing the desired anchoring function. Once the base portion 14 is sufficiently incorporated into the vessel wall 32, additional anchoring, such as that provided by the barb 20, may no longer be needed. If the barb 20 and cannula 21 are formed of resorbable materials, the barb 20 and cannula 21 would be eliminated gradually as the materials of the barb 20 and cannula 21 are absorbed, allowing the incorporated base portion 14 to perform the anchoring function.

As best illustrated in FIGS. 2 and 3, the valve portion 16 is moveable between first and second positions when the valve 10 and cannula 21 are implanted in a body vessel 34. In the first position, illustrated in FIG. 2, the valve portion 16 is positioned within the body vessel 34 so that an opening 46 is formed between the interior surface 40 of the vessel wall 32 and the valve portion 16. Fluid is able to flow through the body vessel 34 at the position of the valve 10 via the opening 46 in the first direction, represented by arrow 48. As such, the valve member 12 can be referred to as being in an open configuration and as permitting fluid flow through the body vessel 34 in the first direction 48.

In the second position, illustrated in FIG. 3, a surface 50 of the valve portion 16 is disposed adjacent a portion of the wall 32 of the body vessel 34. In this configuration, the opening 46 of the first position, described above, is substantially eliminated. Accordingly, the valve member 12 substantially prevents fluid flow through the body vessel 34 in the second, opposite direction, represented by arrow 52. As such, the valve member 12 can be referred to as being in a closed configuration. In this configuration, the cannula 21 allows a controlled amount of retrograde flow, represented by arrows 53, through the valve 10, as described above.

The valve portion 16 can move between the first and second positions, i.e., between open and closed configurations, in response to a change in the direction of fluid flow through a body vessel in which the valve 10 is implanted, such as a change from flow in the first direction 48 to flow in the second, opposite direction 52. Also, the valve portion 16 can move between the first and second positions in response to a change in fluid pressure on one or more sides of the leaflet 12.

Figure 4:
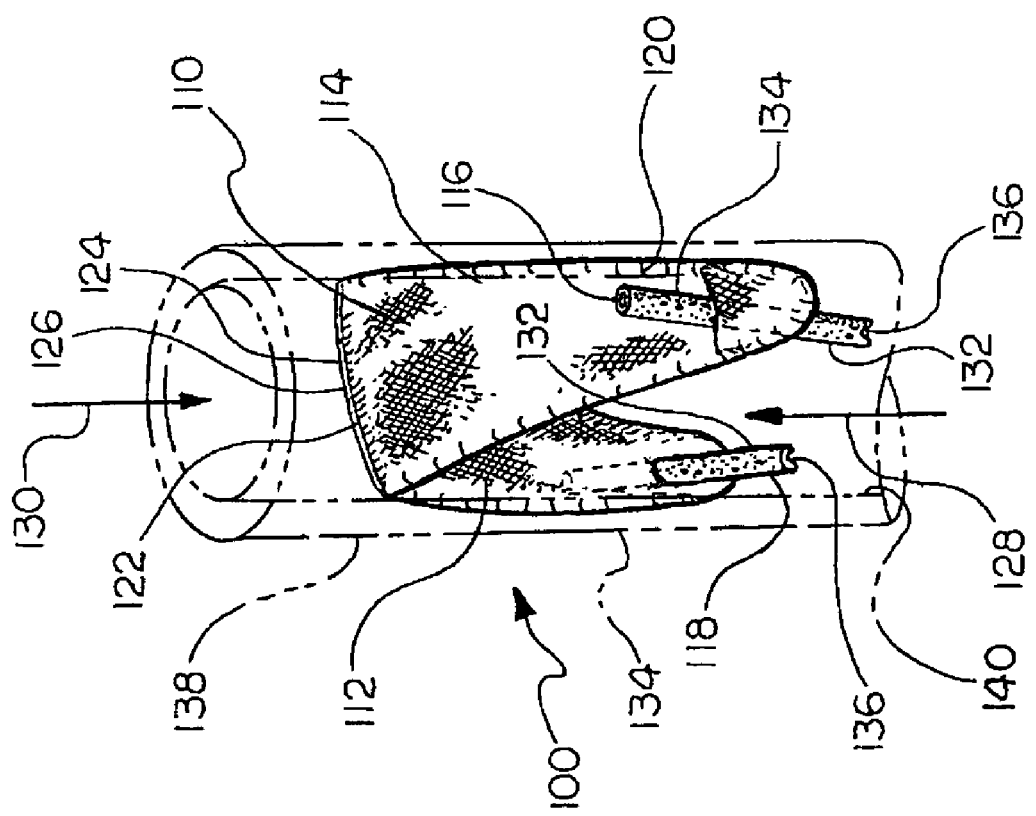
FIG. 4 is a perspective view of a medical device according to a second exemplary embodiment.

FIG. 4 illustrates a medical device 100 according to a second embodiment of the invention. In this embodiment, the device 100 includes two valve member 110, 112 that are attached to a support frame 114. Two cannula 116, 118 are positioned on opposite sides of the medical device 300.

The valve members 110, 112 comprise a section of material, such as a sheet, that is attached to the support frame 114. The valve members 110, 112 can be formed of any suitable material, as described above. The material chosen need only be biocompatible or be able to be made biocompatible.

The valve members 110, 112 can be attached to the support frame 114 in any suitable manner. As illustrated in FIG. 4, sutures 120 or other attachment members can be used to attach the valve members 110, 112 to the support frame 114. Alternatively, the valve members 110, 112 can be attached to the support frame 114 by other means for attaching, such as adhesives, heat sealing, tissue welding, weaving, cross-linking, or any other suitable means for attaching. The specific means for attaching chosen will depend at least upon the materials used in the valve members 110, 112 and the support frame 114.

Each valve member 110, 112 has a free edge 122, 124 that is not attached to the support frame 114. The free edges 122, 124 cooperatively define valve orifice 126. The valve members 110, 112 are both movable between first and second positions. In the first position, the orifice 126 is open and allows fluid flow through the device 100 in a first direction, represented by arrow 128. In the second position, the free edges 122, 124 of valve members 110, 112 come together to close the orifice 126 to substantially prevent fluid flow through the device 100 in a second, opposite direction, represented by arrow 130.

First 116 and second 118 cannulae are disposed on opposite sides of the device 100 and allow a controlled amount of retrograde flow to pass through the medical device 100 when the valve orifice 126 is closed. Each of the cannulae 116, 118 are positioned with a first portion 132 adjacent a side of a valve member 110, 112 that contacts fluid flow in the first direction 128, and a second portion 134 adjacent a side of a valve member 110, 112 that is substantially free of contact with fluid flow in the first direction 374.

In this embodiment, each cannulae 116, 118 includes a recess 136 disposed at one axial end. The recess 136 provides an attachment point at which another device, such as a catheter with a grasping mechanism, can attach to the cannulae 116, 118 for a variety of purposes, such as repositioning and/or removal of the cannulae 116, 118.

The support frame 114 can comprise any suitable support frame. A wide variety of support frames are known in the medical technology arts, and any suitable support frame can be utilized. The specific support frame chosen will depend on several considerations, including the nature of the valve member, the nature of the cannulae, the nature of the point of treatment at which the medical device will be implanted, and the condition for which the medical device is being used to treat. The support frame 114, if included, need only provide a surface to which the valve member can be attached.

The support frame 114 advantageously has radially compressed and radially expanded configurations. Such a support frame 114 can be implanted at a point of treatment within a body vessel 138 by minimally invasive techniques, such as via delivery and deployment with an intravascular catheter. The support frame 114 can optionally provide additional function to the medical device 100. For example, the support frame 114 can provide a stenting function, i.e., exert a radially outward force on the interior wall 140 of the vessel 138 in which the medical device 100 is implanted. By including a support frame 114 that exerts such a force, a medical device according to the invention can provide both a stenting and a valving function at a point of treatment within a body vessel 138.

The support frame 114 can be self-expandable or balloon expandable. The structural characteristics of both of these types of support frames are known in the art, and are not detailed herein. Each type of support frame has advantages and, for any given application, one type may be more desirable the other based on a variety of considerations. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, medical devices according to the invention intended for implantation in the peripheral vasculature, such as prosthetic venous valves, advantageously include a self-expandable support frame. These support frames, as known in the art, are generally more flexible than balloon-expandable support frames following deployment.

The support frame 114 can be formed of any suitable material and need only be biocompatible or able to be made biocompatible. The support frame 114 should be made from a resilient material, preferably metal wire formed from stainless steel or a superelastic alloy, such as nitinol. While round wire is depicted in FIG. 4, other types, such as flat, square, triangular, D-shaped, and delta-shaped wire, may be used to form the frame 114. Other examples of suitable materials include, without limitation, stainless steel, nickel titanium (NiTi) alloys, e.g., nitinol, other shape memory and/or superelastic materials, polymers, and composite materials. Also, resorbable and bioremodellable materials can be used, including the resorbable and bioremodellable materials described herein.

Figure 5:
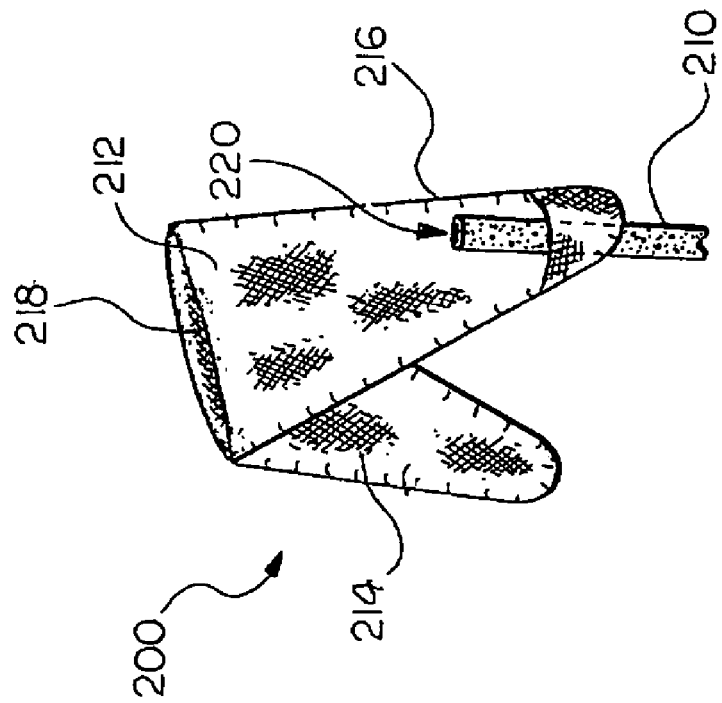
FIG. 5 is a perspective view of a medical device according to a third exemplary embodiment.

FIG. 5 illustrates a medical device 200 according to a third embodiment of the invention. The device 200 of this embodiment is similar to the device illustrated in FIG. 4, except that the device 200 includes only one cannula 210. Thus, the device includes first 212 and second 214 valve members attached to a support frame 216. The valve members 212, 214 cooperatively define a valve opening 218 that opens and closes to regulate fluid flow through a body vessel. The cannula 210 allows a controlled amount of retrograde flow through the device 200, represented by arrow 220.

Figure 6:
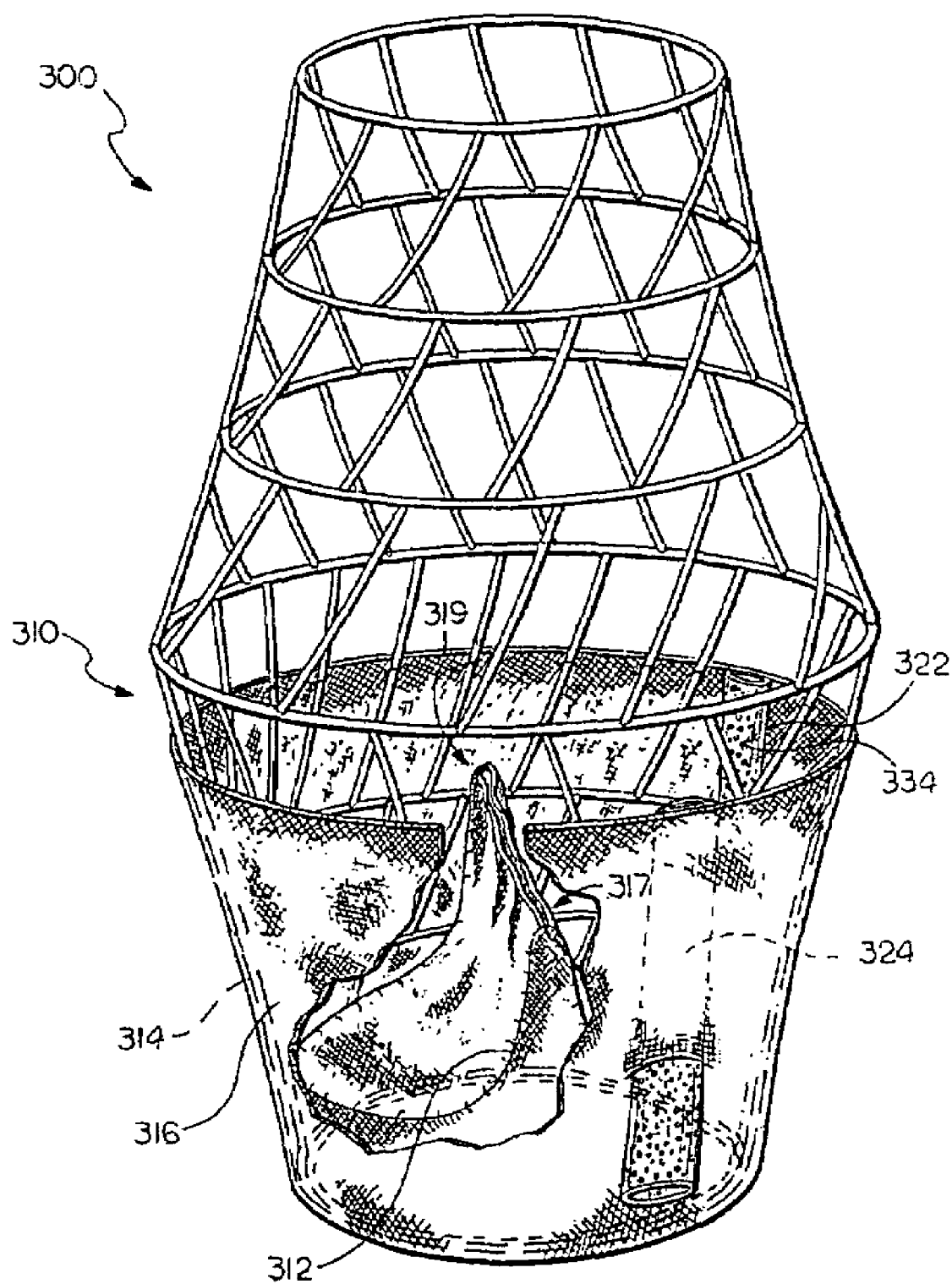
FIG. 6 is a perspective view of a medical device according to a fourth exemplary embodiment.

FIG. 6 illustrates a fourth exemplary embodiment. The medical device 300 according to this embodiment is similar in material construction to the valves illustrated in FIGS. 4 and 5 as described above. The medical device 300 according to this embodiment is a prosthetic valve 310 for regulating fluid flow through a body vessel. The device 300 comprises a first tubular frame member 312 and a second tubular frame member 314 disposed circumferentially around the first tubular frame member 312. A tubular valve member 316 is disposed about a portion of the second tubular frame member 314 and into a space between the frame members 312, 314. Opposing sides of one end 317 of the valve member 316 collapse onto the first tubular member 312 to close an opening 319 defined by the end of the valve member 316 and provide a valving function. First 322 and second 324 cannulae are disposed adjacent a surface of the valve member 316.

In the illustrated embodiment, each of the cannulae 322, 324 are positioned on one side of the device 300. It is noted, however, that any suitable relative positioning of the cannulae 322, 324 can be used.

In this embodiment, the cannulae 322, 324 define a plurality of pores 334. The pores 334 can have any suitable size that allows for an amount of retrograde flow, and the pores 334 do not necessarily have to be uniform in size. The pores 334, are advantageously sized to allow passage of the fluid and cellular components of blood.

Figure 7:
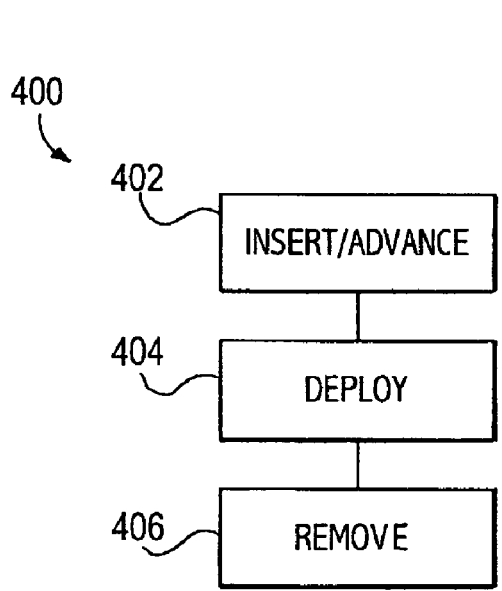
FIG. 7 is a block diagram of a method according to one embodiment of the invention.

FIG. 7 illustrates a method 400 of delivering medical devices and cannulae into a body vessel according to one embodiment of the invention. In a first step 402, an intraluminal medical device with attached cannulae is advanced to a first point of treatment (POT). Preferably, this step comprises advancing a delivery assembly, that includes a sheath and a carrier including the intraluminal medical device through a body vessel. In another step 404, the first intraluminal medical device with attached cannulae is deployed.

The manner in which this step is accomplished will depend on the arrangement of the intraluminal medical device within the delivery device. For example, if the intraluminal medical device is disposed on an elongate carrier, the intraluminal medical device can be deployed by withdrawing the sheath to expose the intraluminal medical device. If, however, the intraluminal medical device is not disposed on an elongate carrier member and is simply contained within a lumen of the delivery device independent of a carrier, the intraluminal medical device can be deployed simply by forcing the medical device out of an end of a lumen. For example, if the intraluminal medical device is contained within a carrier, an obturator can be used to force the intraluminal medical device out of a delivery device. These delivery devices are intended only to serve as examples of the invention, and not to limit the scope of the method of delivery, or its protection, in any manner. Many delivery devices are known in the art and any suitable delivery device may be utilized to deliver the intraluminal medical device In another step 406, the delivery device is removed from the body vessel.

Figure 8:
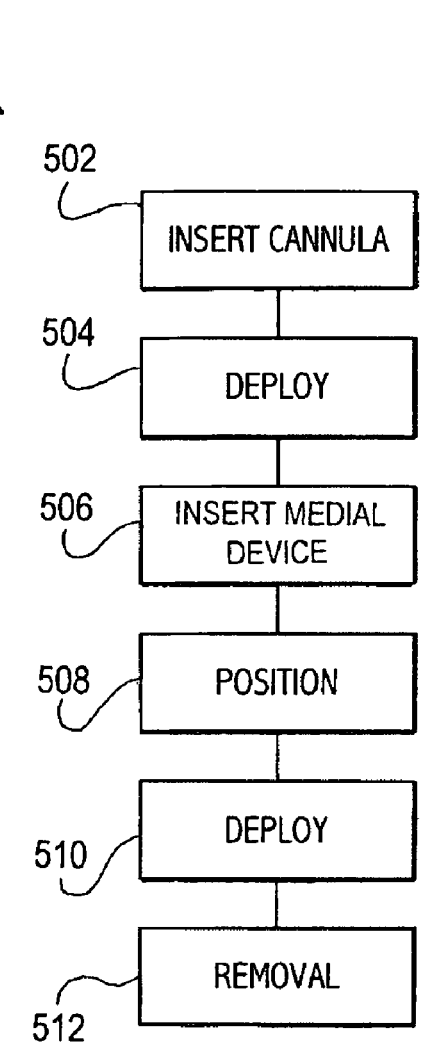
FIG. 8 is a block diagram of a method according to another embodiment of the invention.

FIG. 8 illustrates a method 500 of delivering medical devices and cannulae into a body vessel according to another embodiment of the invention. In a first step 502, at least one cannula is advanced to a first point of treatment (POT). Preferably, this step comprises advancing a delivery assembly, such as an assembly that includes a sheath and a carrier including the at least one cannula through a body vessel. However, many delivery devices are known in the art and any suitable delivery device is acceptable.

In another step 504, the at least one cannula is deployed. The manner in which this step is accomplished will depend on the arrangement of the at least one cannula within the delivery device.

In another step 506, an intraluminal medical device is advanced through the delivery device. This step is accomplished after deployment of the at least one cannula, and the manner in which this step is accomplished will also depend upon the configuration of the intraluminal medical device. For example, if an elongate carrier is utilized, the elongate carrier is advanced through the lumen of the delivery device. However, if a housing carrier is utilized, the intraluminal medical device is advanced through the lumen of the delivery device via an obturator. Preferably, the advancement of the second intraluminal medical device is accomplished only after removal of any advancement means used to advance the at least one cannula, such an elongate carrier or an obturator.

In another step 508, the intraluminal medical device is positioned at the POT in the body vessel adjacent or near the at least one cannula. The intraluminal medical device can be positioned with respect to the at least one cannula so that a first portion of the at least one cannula is on the side of the valve in contact with the fluid flow in a first direction, and a second portion of the at least one cannula is on the other side of the valve in contact with the fluid flow in a second, opposite direction. In another step 510, the intraluminal medical device is deployed. Again, the mechanism of deploying the intraluminal medical device will depend on the configuration of the medical device and carrier, as described above.

In another step 512, the delivery device is removed from the body vessel.

Figure 9:
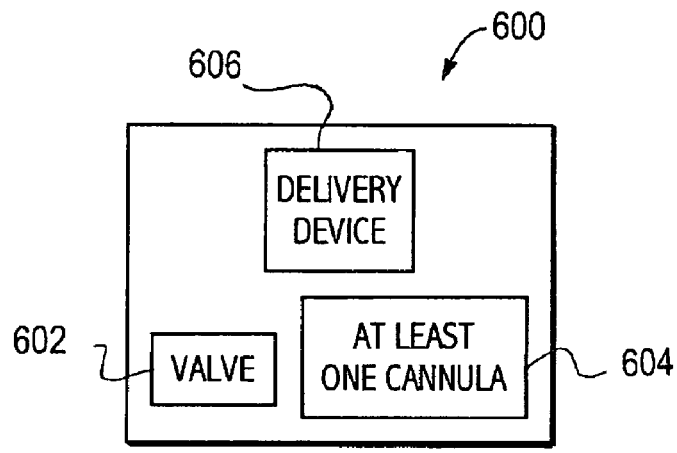
FIG. 9 is a schematic of a kit and its components according to an embodiment of the invention.

FIG. 9 illustrates the components of a kit 600 according to another embodiment of the invention. The kit 600 includes an intraluminal medical device 602, such as a prosthetic valve, and at least one cannula 604. The kit could also include any suitable delivery device 606 for the delivery of the intraluminal medical device 602.

While the kit 600 illustrated herein contains only one intraluminal medical device 602 and only cannula 604, it is contemplated that any suitable number of additional intraluminal medical devices and cannulae can be used. The actual number chosen will depend on several factors, including the number of POTs in any single body vessel and the number of cannulae necessary for the particular embodiment of the intraluminal medical device.

In all embodiments of the present invention, the intraluminal medical device can comprise any suitable intraluminal medical device that may be used in conjunction with cannula that allow for retrograde fluid flow. The intraluminal medical device can comprise a self-expanding or balloon expandable device. In exemplary embodiments of the invention, the intraluminal medical device comprises a prosthetic valve, such as a prosthetic venous valve. Any suitable prosthetic valve can be utilized in the devices and methods according to the present invention. Examples of suitable prosthetic venous valves include those described in U.S. Pat. No. 6,508,833 to Pavcnik et al. for a MULTIPLE-SIDED INTRALUMINAL MEDICAL DEVICE, and published U.S. Patent Application 2001/0039450 to Pavcnik et al. for an IMPLANTABLE MEDICAL DEVICE. Other suitable prosthetic venous valves include stentless prosthetic venous valves, such as the valves described in commonly-owned Provisional Patent Application Ser. No. 60/459,475, filed on Apr. 1, 2003, and entitled Percutaneously Deployed Vascular Valve With Wall-Adherent Adaptations. Each of these references are hereby incorporated into this disclosure in their entirety for the express purpose of describing suitable implantable medical devices for use in and with the devices, kits, and methods according to the present invention.

It may be desirable to deploy different types of intraluminal medical devices with cannula designed to allow retrograde fluid flow in a single procedure and/or vessel. For example, it may be desirable to deploy a prosthetic venous valve at one location in a vessel, and deploy a self-expandable stent at another location in the same vessel. Thus, any suitable combination of intraluminal medical devices can be used in the kits and methods of the present invention. The exact combination and number of intraluminal medical devices used in any particular method or included in any particular kit will depend on various factors, including the condition being treated.

The foregoing detailed description provides exemplary embodiments of the invention and includes the best mode for practicing the invention. These embodiments are intended only to serve as examples of the invention, and not to limit the scope of the invention, or its protection, in any manner.

We claim:

1. An implantable medical device for regulating fluid flow through a body vessel, said implantable medical device comprising:
   a valve member moveable within said body vessel between a first position that permits said fluid flow in a first direction and a second position that substantially prevents said fluid flow in a second direction;
   at least one cannula disposed adjacent the valve member and adapted to permit a controlled amount of said fluid flow through said implantable medical device in the second direction; and
   means for maintaining an axial position of the valve member within said body vessel;
   wherein the valve member defines an opening and the means for maintaining an axial position of the valve member within said body vessel comprises a barb at least partially disposed within the opening and through the valve member.

2. An implantable medical device according to claim 1, wherein the means for maintaining an axial position of the valve member within said body vessel comprise an expandable support frame connected to the valve member.

3. An implantable medical device according to claim 1, wherein the valve member comprises a remodellable material.

4. An implantable medical device according to claim 3, wherein the at least one cannula comprises a resorbable material.

5. An implantable medical device according to claim 1, wherein the valve member comprises an extracellular matrix material.

6. An implantable medical device according to claim 1, wherein the valve member comprises small intestine submucosa.

7. An implantable medical device according to claim 1, wherein the at least one cannula defines one or more pores.

8. An implantable medical device according to claim 1, wherein the at least one cannula is formed of a resorbable material.

9. An implantable medical device according to claim 1, wherein the at least one cannula comprises an antithrombogenic agent.

10. An implantable medical device according to claim 1, wherein the at least one cannula comprises first and second cannulae.

11. An implantable medical device for regulating fluid flow through a body vessel, said implantable medical device comprising:
    an expandable support frame having radially compressed and radially expanded configurations;
    at least one valve member attached to the expandable support frame, the at least one valve member including at least a portion that is moveable between a first position that permits said fluid flow in a first direction and a second position that substantially prevents said fluid flow in a second direction;
    a cannula disposed adjacent the at least one valve member and adapted to permit a controlled amount of said fluid flow through said implantable medical device in the second directions
    wherein the at least one valve member comprises a remodellable material; and
    wherein the cannula comprises a resorbable material.

12. An implantable medical device according to claim 11, wherein the cannula passes through the at least one valve member.

13. An implantable medical device according to claim 12, wherein the cannula includes a first portion disposed adjacent a first side of the valve member and a second portion disposed adjacent a second side of the valve member.

14. An implantable medical device according to claim 11, wherein the cannula has a substantially circular cross-sectional shape.

15. An implantable medical device according to claim 11, wherein the cannula has a substantially ovoid cross-sectional shape.

16. An implantable medical device for regulating fluid flow through a body vessel, said implantable medical device comprising:
    an expandable support frame having radially compressed and radially expanded configurations;
    a first valve member attached to the expandable support frame and moveable between first and second positions;
    a second valve member attached to the expandable support frame and moveable between third and fourth positions, the second valve member cooperating with the first valve member to define a valve opening that selectively opens and closes with movement of the first and second valve members to permit and substantially prevent fluid flow through said implantable medical device;
    a first cannula disposed through the first valve member and adapted to permit a first controlled amount of fluid flow through said implantable medical device; and
    a second cannula disposed through the second valve member and adapted to permit a second controlled amount of fluid flow through said implantable medical device;
    wherein at least one of the first and second valve members comprises a remodellable material; and
    wherein at least one of the first and second cannulae comprises a resorbable material.

* * * * *